(12) United States Patent
McGall et al.

(10) Patent No.: US 9,085,761 B1
(45) Date of Patent: Jul. 21, 2015

(54) METHODS AND COMPOSITIONS FOR AMPLIFICATION OF NUCLEIC ACIDS

(71) Applicant: Affymetrix, Inc., Santa Clara, CA (US)

(72) Inventors: Glenn H. McGall, Palo Alto, CA (US);
Anthony D. Barone, San Jose, CA (US);
Christopher J. Kubu, Twinsburg, OH (US)

(73) Assignee: AFFYMETRIX, INC., Santa Clara, CA (US)

( * ) Notice: Subject to any disclaimer, the term of this patent is extended or adjusted under 35 U.S.C. 154(b) by 146 days.

(21) Appl. No.: 13/791,164

(22) Filed: Mar. 8, 2013

Related U.S. Application Data (60) Provisional application No. 61/659,542, filed on Jun. 14, 2012.

(51) Int. Cl.
| | | |
|---|---|---|
| C12Q 1/00 | (2006.01) | |
| C12Q 1/68 | (2006.01) | |
| C12P 19/34 | (2006.01) | |
| C12N 9/12 | (2006.01) | |

(52) U.S. Cl.
CPC ............... *C12N 9/1241* (2013.01); *C12P 19/34* (2013.01); *C12Q 1/6869* (2013.01)

(58) Field of Classification Search
CPC ........................... C12Q 1/6869; C12N 9/1241
USPC .............................................. 435/4, 6.12, 91.1
See application file for complete search history.

(56) References Cited

U.S. PATENT DOCUMENTS

| | | |
|---|---|---|
| 3,740,421 A | 6/1973 | Schmolka et al. |
| 4,683,195 A | 7/1987 | Mullis et al. |
| 4,683,202 A | 7/1987 | Mullis |
| 4,800,159 A | 1/1989 | Mullis et al. |
| 5,338,671 A | 8/1994 | Scalice et al. |
| 5,411,876 A | 5/1995 | Bloch et al. |
| 5,677,152 A | 10/1997 | Birch et al. |
| 5,736,333 A | 4/1998 | Livak et al. |
| 5,773,258 A | 6/1998 | Birch et al. |
| 6,127,155 A | 10/2000 | Gelfand et al. |
| 6,242,235 B1 | 6/2001 | Shultz et al. |
| 6,818,437 B1 | 11/2004 | Gambini et al. |
| 2002/0168658 A1 | 11/2002 | Weissman et al. |

(Continued)

FOREIGN PATENT DOCUMENTS

WO      2008/152102 A1    12/2008

OTHER PUBLICATIONS

BASF Corporation, Tetronic 1107 Block Copolymer Surfactant Technical Bulletin, 2004, Florham Park, New Jersey.

(Continued)

*Primary Examiner* — Jezia Riley
(74) *Attorney, Agent, or Firm* — Pearne & Gordon LLP (57) ABSTRACT

The present invention provides methods, compositions, and kits for storing and enhancing the activity of polymerases and particularly thermostable polymerases. The methods comprise mixing a thermostable polymerase with at least one zwitterionic or ylide surfactant that has at least one PEO group. In another aspect the polymerase is mixed with a blocker such as PLURONIC® or TETRONIC® or an amine N-oxide derivative thereof. The thermostable polymerase may be reversibly inactivated by treatment with 2-(Methylsulfonyl)ethyl 4-nitrophenyl carbonate. Compositions and kits for performing the process according to the invention are also provided.

10 Claims, 6 Drawing Sheets

(56) References Cited

U.S. PATENT DOCUMENTS

| | | |
|---|---|---|
| 2003/0017567 A1 | 1/2003 | Parthasarathy et al. |
| 2008/0064071 A1 | 3/2008 | Hogrefe et al. |
| 2008/0145910 A1 | 6/2008 | Ward et al. |
| 2010/0099150 A1 | 4/2010 | Fang et al. |
| 2011/0044929 A1 | 2/2011 | Reddington et al. |

OTHER PUBLICATIONS

BASF Corporation, Tetronic 1107 Micropastille Safety Data Sheet, Version 1.1, Dec. 15, 2006, Florham Park, New Jersey.

Chou, Q. et al., "Prevention of pre-PCR mis-priming and primer dimerization improves low-copy-number. amplifications," Nucleic Acids Research, vol. 20, No. 7, 1992, 1717-1723.

Neugebauer, J.M., "Detergents: an Overview," Methods in Enzymology, vol. 182, 1990, 239-253.

Rittie, L and Perbal, B., "Enzymes used in molecular biology: a useful guide," Journal of Cell Communication and Signaling, vol. 2, 2008, 25-45.

Rosen, M.J., Surfactants and Interfacial Phenomena, 3rd Edition, 2004, John Wiley & Sons, Inc., Hoboken, NJ.

Schwarz, K. et al., "Improved yields of long PCR products using gene 32 protein," Nucleic Acids Research, vol. 18, No. 4, 1990, 1079.

Wu, A.M. and Cetta, A., "On the Stimulation of Viral DNA Polymerase Activity by Nonionic Detergent," Biochemistry, vol. 14, No. 4, 1975, 789-795.

METHODS AND COMPOSITIONS FOR AMPLIFICATION OF NUCLEIC ACIDS

CROSS-REFERENCE TO RELATED APPLICATIONS

This application claims the benefit of U.S. Provisional Patent Application Ser. No. 61/659,542, filed Jun. 14, 2012, the contents of which are incorporated herein by reference.

FIELD OF THE INVENTION

The present invention is generally in the field of nucleic acid amplification.

BACKGROUND OF THE INVENTION

Compositions of thermostable nucleic acid polymerases are useful for amplification of nucleic acids by multiple cycles of the polymerase chain reaction. Various compositions for stabilizing polymerases using surfactants have been disclosed. In an early study it was observed that viral DNA polymerase activity was stimulated and stabilized against thermal inactivation by nonionic detergent (see, Wu and Cetta, Biochemistry (1975) 14(4):789-795). U.S. Pat. No. 6,127,155 discloses stabilization of thermostable DNA polymerases in a composition containing non-ionic polymeric detergents. U.S. Pat. No. 6,242,235 discloses cationic polyethoxylated amine surfactants as polymerase stabilization agents, WO 2008152102 (Liu et al.) and US Pat. Pub. No. 20100099150 (Fang et al.) disclose polymerase stabilization by anionic detergents. US Pat. Pub. No. 20080064071 (Hogrefe et al.) discloses zwitterionic detergents for storage and use of DNA polymerases and US Pat. Pub. No. 2008145910 (Ward et al.) discloses stabilization of DNA polymerase using anionic or zwitterionic detergents during thermal cycling.

Amplification of nucleic acids involves the thermal cycling of a reaction mixture containing a nucleic acid polymerase to generate an amplified target nucleic acid. An example of this thermal cycling process is that which occurs in Polymerase Chain Reaction (PCR), a laboratory technique that can theoretically take one molecule of DNA and produce measurable amounts of identical DNA in a short period of time. PCR is a widely used method in the fields of biotechnology, forensics, medicine, and genetic research. In this method, oligonucleotides are used as primers for a series of synthetic reactions that are catalyzed by a DNA polymerase. The reaction mixture is subjected to multiple cycles of denaturation, annealing, and synthesis performed at different temperatures. Thermostable polymerases are generally used to amplify the target nucleic acid sequences in these thermal cycling reactions because they are not inactivated by the heat denaturation step and, therefore, do not need to be replaced in every round of the amplification cycle. Although efficient, exponential amplification of target sequences is not an unlimited process. Under normal reaction conditions, the amount of DNA polymerase becomes limiting after a certain number of cycles of amplification.

Attempts have been made to improve the PCR amplification process by employing detergents and/or surfactants. For example, U.S. Pat. No. 6,127,155 discloses that the non-ionic detergents NP-40 and Tween stabilize Taq DNA polymerase. However, this patent does not disclose the use of non-detergent surfactants or zwitterionic detergents for the stability of thermostable polymerases in PCR reactions. As another example, US Pat. Pub. No. 20030017567 discloses a method for performing an amplification reaction utilizing a dye that converts electromagnetic energy into thermal energy to heat the reaction mixture. A zwitterionic surfactant is added to the reaction mixture to reduce interference of the dye with the functioning of the nucleic acid polymerase. Additionally, U.S. Pat. Pub. No. 20020168658 discloses the use of zwitterions in combination with a compound that disrupts base pairing, e.g., DMSO, to improve the amplification of nucleic acids that are G+C rich. However, this publication does not disclose the use of zwitterionic detergents alone in improving the amplification of nucleic acids and actually teaches that the zwitterionic detergents used should be selected carefully so as not to inhibit the activity of the DNA polymerase in the reaction.

Given the widespread use and importance of thermal cycling processes, there is a need in the art for ways to improve the stability and/or enhance the activity of thermostable enzymes used in DNA amplification.

SUMMARY OF THE INVENTION

In one aspect, stabilization of nucleic acid polymerases by zwitterionic derivatives of poly-alkoxylated alkyl derivatives and particularly amine-N-oxide derivatives is disclosed. Amine-N-oxide surfactants containing a fatty alkyl group, that is preferably linear, and one or more polyoxyethylene groups are particularly preferred for stabilizing polymerase activity.

In another aspect, stabilization of nucleic acid polymerases by nonionic poly(propylene oxide)-poly(ethylene oxide) block copolymer surfactants is disclosed.

In another aspect, stabilization of nucleic acid polymerases by cationic poly(propylene oxide)-poly(ethylene oxide) block copolymer surfactants based on ethylenediamine is disclosed.

In another aspect, a thermostable polymerase that has been modified with 2-(Methylsulfonyl)ethyl 4-nitrophenyl carbonate (MSEC) is disclosed. This modification inactivates the polymerase so that it is inactive until incubated at temperatures greater than about 50° C. for at least 10 minutes.

In another aspect, compositions including a thermostable polymerase that has been modified with MSEC and an ylide surfactant are disclosed.

DETAILED DESCRIPTION

Unless defined otherwise, all technical and scientific terms used herein have the same meaning as commonly understood by one of ordinary skill in the art to which the invention pertains. The following definitions supplement those in the art and are directed to the current application and are not to be imputed to any related or unrelated case, e.g., to any commonly owned patent or application. Although any methods and materials similar or equivalent to those described herein can be used in the practice for testing of the present invention, the preferred materials and methods are described herein. Accordingly, the terminology used herein is for the purpose of describing particular embodiments only, and is not intended to be limiting.

As used in this specification and the appended claims, the singular forms "a," "an" and "the" include plural referents unless the context clearly dictates otherwise. Thus, for example, reference to "a molecule" includes a plurality of such molecules, and the like.

The term "about" as used herein indicates the value of a given quantity varies by +/−10% of the value, or optionally +/−5% of the value, or in some embodiments, by +/−1% of the value so described.

Throughout this disclosure, various aspects of this invention can be presented in a range format. It should be understood that when a description is provided in range format, this is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6, for example, as well as individual numbers within that range, for example, 1, 2, 3, 4, 5, and 6. This applies regardless of the breadth of the range.

Many of the methods and systems disclosed herein utilize enzyme activities. A variety of enzymes are well known, have been characterized and many are commercially available from one or more supplier. For a review of enzyme activities commonly used in molecular biology see, for example, Rittie and Perbal, *J. Cell Commun. Signal.* (2008) 2:25-45, incorporated herein by reference in its entirety.

There are a variety of methods for amplification that may be used in combination with the methods disclosed herein include. Amplification of nucleic acids is widely used in research, forensics, medicine and agriculture. One of the best-known amplification methods is the polymerase chain reaction (PCR), (See for example, U.S. Pat. Nos. 4,683,195, 4,683,202 and 4,800,159). A PCR reaction typically utilizes two oligonucleotide primers, which are hybridized to the 5' and 3' borders of the target sequence and a DNA polymerase, which can extend the annealed primers by adding on deoxynucleoside-triphosphates (dNTPs) to generate double-stranded products. By raising and lowering the temperature of the reaction mixture, the two strands of the DNA product are separated and can serve as templates for the next round of annealing and extension, and the process is repeated.

The invention provides compositions, kits and methods that include a polymerase and a zwitterionic or non-ionic surfactant that may be a detergent or non-detergent. Such compositions and methods are useful in, among other things, the storage and use of DNA polymerases in thermal cycling reactions, including, but not limited to PCR and all of its variants (e.g., real-time PCR or quantitative PCR). The present invention identifies novel surfactants that increase stability and enhance activity of thermostable DNA polymerases.

It has been previously observed that product yields are dramatically higher when PCR amplification reactions are conducted in buffers containing one or more non-ionic detergents (NP-40, TWEEN-20), zwitterionic detergents (e.g., CHAPS, CHAPSO, Anzergent 3-10, and Anzergent 3-12) or non-detergent surfactants (e.g., Surfynol 465). Similarly, detergents and non-detergent surfactants are known to produce higher amplification efficiencies, higher total fluorescence, and earlier Ct values in QPCR reactions employing thermostable DNA polymerase and SYBR Green to monitor duplex DNA formation.

In general, the invention is directed to storage and reaction compositions having a polymerase and at least one surfactant. In one embodiment, the storage and reaction compositions comprise a polymerase and two or more surfactants. Generally, a reaction mixture will include some or all of the necessary components to perform a nucleic acid synthesis reaction, such as primers, dNTPs, and buffers. A storage mixture may or may not include all the components necessary to perform a nucleic acid synthesis reaction.

The polymerases may be stored in a storage buffer comprising a zwitterionic detergent, which may be an ylide, a non-detergent surfactant, or both. The polymerases of the invention, described herein, may be obtained commercially or produced by methods well known to one of skill in the art. The storage buffer and reaction buffers may include from about 0.001% to 5% volume/volume of each zwitterionic detergent or non-detergent surfactant employed.

The terms "surfactant" as used herein refers to compounds that are amphiphilic, meaning they contain both hydrophobic groups (their tails) and hydrophilic groups (their heads). Surfactants lower the surface tension of a liquid, the interfacial tension between two liquids, or that between a liquid and a solid. Surfactants may act as detergents, wetting agents, emulsifiers, foaming agents, and dispersants. The terms surfactant and detergent may be used interchangeably herein, but detergents typically have the additional quality of having cleaning properties in dilute solution. Surfactants or detergents may be anionic, (e.g. alkylbenzenesulfonates), cationic, non-ionic (e.g. Tween, Triton and Brij series detergents) and zwitterionic (e.g. CHAPS).

The term "ylide" or "ylides" refers to a subset of zwitterionic compounds in which an anionic site Y− is attached directly to a heteroatom X+ (usually nitrogen, phosphorus or sulfur) carrying a formal positive charge. They are thus 1,2-dipolar species of the type RmX+—Y—Rn. If X is a saturated atom of an element from the first row of the periodic system, the ylide is commonly represented by a charge-separated form. If X is a second, third, etc. row element uncharged canonical forms are available RmX=YRn. If X is an unsaturated atom, doubly bonded to another first row element Z, the negative charge on Y may be stabilized by p-conjugation, Z=X+—Y—Rn<<Z—X+=YRn. Such ylides belong to the class 1,3-dipolar compounds. Note that ylide is a complete word, not to be confused with the suffix -ylide, used for some radical anions. Subclasses of ylides: Ylides RmX+—C—R2 having the negative charge on carbon are classified by citing the name of the element X before the word ylide. For example, nitrogen ylide, phosphorus ylide, oxygen ylide, and sulfur ylide. A further specification may be achieved by citing the class name of RmX before the word ylide. Thus nitrogen ylides include amine ylides, R3N+—C—R2, azomethine ylides, R2C=N+R—C—R2, and nitrile ylides, RC°N+—C—R2.

A "zwitterion" is a neutral compound having formal unit electrical charges of opposite sign, for example, $H_3N^+CH_2C(=O)O^-$ ammonioacetate (glycine). The compound betaine $((CH_3)_3N^+-CH_2C(=O)O^-$ N,N,N-trimethylammonioacetate) and other "betaines" (neutral molecules having charge-separated forms with an onium atom which bears no hydrogen atoms and that is not adjacent to the anionic atom) are also zwitterionic compounds. As used herein the term refers to compounds with the charges on either adjacent or non-adjacent atoms. Zwitterionic compounds with charges on adjacent atoms may also be referred to herein as ylides. Such compounds include, but are not limited to, CHAPS and sulfobetaines sold under the brand names ZWITTERGENT® (Calbiochem, San Diego, Calif.) and ANZERGENT® (Anatrace, Inc., Maumee, Ohio).

An "amine oxide" or "amine N-oxide" is a compound derived from tertiary amines by the attachment of one oxygen atom to the nitrogen atom $R_3N^+-O^-$. By extension the term includes the analogous derivatives of primary and secondary amines. Because the charges are on adjacent atoms, amine oxides are considered to be ylides herein.

In some aspects, zwitterionic or ylide derivatives of polyalkoxylated alkyl derivatives, particularly the amine N-oxides are used to stabilize polymerases. These surfactants have the following general characteristics: a hydrophobic group comprising a linear alkyl or poly(propylene oxide) chain; a hydrophilic polyether group comprising a poly(ethylene oxide) or a random copolymer of polyethylene oxide/poly(propylene oxide); and an ylide or zwitterionic group comprising an amine oxide, carboxy-alkylammonium, or sulfo-alkylammonium.

In other aspects, the surfactant is block co-polymer that may be a poloxamer or a poloxamine. The term "block co-polymer" herein refers to a polymer composed of two or more different polymers ("co-polymer") arranged in segments or "blocks" of each constituent polymer. Both poloxamers and poloxamines are block copolymers.

The term "poloxamer" herein refers to any di- or tri-block copolymer composed of polypropylene oxide and polyethylene oxide blocks arranged in a basic A-B-A structure: $PEO_x$-$PPO_y$-$PEO_x$. Polypropylene oxide (PPO or polyoxypropylene, also (poly(propylene oxide))) has the formula $(C_3H_6O)_x$, (thus a subunit mw of 58) and is a hydrophobe. Polyethylene oxide (PEO or polyoxyethylene) is a nonionic homopolymer of ethylene oxide and can be represented by the formula $(OCH_2CH_2)_x$ where x represent the average number of oxyethylene groups, it may also be represented by the formula $(C_2H_4O)_x$, (thus a subunit mw of 44) and is a hydrophile. Poloxamers are nonionic and have a central hydrophobic chain of PPO flanked by two hydrophilic chains of PEO. For a more comprehensive description see U.S. Pat. No. 3,740,421. The common chemical name for poloxamers is polyoxypropylene-polyoxyethylene block copolymer. The CAS number is 9003-11-6.

There are many species of poloxamers differing in total molecular weight, polyoxypropylene to polyoxyethylene ratio, surfactant properties and physical form in undiluted solution. Physical forms include Liquids (L), Pastes (P) and Flakable solids (F). The manner in which poloxamers are typically synthesized results in a population of molecules in a relatively circumscribed range of molecular weights characterized by a hydrophobe having a defined average molecular weight and total average percentage of hydrophile groups. Because the lengths of the polymer blocks can be customized, many different poloxamers exist with slightly different properties. Properties include, for example, hydrophilic-lipophilic balance or HLB and cloud point.

Poloxamers are also known by the trade name PLURONIC® in the US and LUTROL® in Europe (BASF). BASF developed a PLURONIC® grid to provide a graphic representation of the relationship between copolymer structure, physical form and surfactant characteristics. On the PLURONIC® surfactant grid the molecular weight ranges of the PPO are plotted against the weight-percent of the PEO present in each molecule. Poloxamer species defined by their location on the PLURONIC® grid can be expected to have shared properties that are a function of their total molecular weight and relative hydrophobicity. For a description of the PLURONIC® grid and an explanation of the nomenclature used by BASF in naming PLURONICS® see US Pat. Pub. No. 20110044929.

Copolymers with a short hydrophilic poly-PEO block or/and an extended lipophilic poly-PPO block (such as PLURONIC® L121 and L101) are highly lipophilic and are characterized by a relatively low CMC and low HLB. In contrast, copolymers with an extended hydrophilic poly-PEO block or/and short lipophilic poly-PPO block (such as PLURONIC® F108 and F88) are hydrophilic and are characterized by relatively high CMC and high HLB. PLURONIC® compositions such as P85 or P103 are intermediate in their lipophilicity and have CMC and HLB values that fall between the two extremes identified above.

As used herein, the term "poloxamine" refers to poly(oxyethylene)-poly(oxypropylene) (PEO-PPO) block copolymers where a PEO-PPO unit is linked to another PEO-PPO unit by an amine and having the general structure $(PEO_n\text{-}PPO_m)_2\text{-}N\text{-}C_2H_4\text{-}N\text{-}(PPO_m\text{-}PEO_n)\text{-}_2$. TETRONIC® and TETRONIC® R nonionic surfactants produced by BASF are exemplary poloxamines.

Poloxamines are in the alkoxylated amine chemical family and have a hydrophobic center consisting of two tertiary amino groups carrying both two hydrophobic PPO chains of equal length each followed by a hydrophilic PEO chain. Poloxamines can still be described as a tri-block copolymer although bulkier than poloxamers. Poloxamines of the BASF TETRONIC® type have the chemical name: 1,2-Ethanediamine, polymer with the and the CAS number: 11111-34-5. Reverse TETRONICS® have the formula $(PPO_n\text{-}PEO_m)_2\text{-}N\text{-}C_2H_4\text{-}N\text{-}(PEO_m\text{-}PPO_n)_2$ and the CAS number: 26316-40-5.

In another aspect polymerases are stabilized by inclusion of poly-alkoxylated alkylamine derivatives, particularly amine N-oxides. Although alkyl ($C_8$-$C_{18}$)-dimethylamine N-oxides are commonly available, we did not observe them to be effective for polymerase stabilization. On the other hand amine oxide detergents containing a fatty alkyl group (preferably linear) and one or more polyoxyethylene groups were observed to be particularly effective for stabilizing polymerase activity. The following general structures are exemplary of the compounds found to be effective for polymerase stabilization:

(I)

where $Q=\text{—}O^\ominus$ or $\text{—}X\text{—}Y$; where $X=C_1\text{-}C_3$ alkyl; and $Y=CO_2^\ominus$, $SO_3^\ominus$;
m+n=2-200 and more preferably 5-50;
R1=$C_1$-$C_{30}$ alkyl and more preferably $C_{10}$-$C_{20}$;
R2=$CH_3$, $CH_2CH_3$; x=1, 2; and
R3=H, $CH_3$, or $CH_2OH$.

In another aspect polymerases are stabilized using ylide or zwitterionic surfactants derived from alkanediamine block copolymers (for example TETRONIC® surfactants). The following structures are exemplary:

(II)

Q=—O$^\ominus$; or —X—Y; where X=C$_1$-C$_3$ alkyl; and Y=CO$_3^\ominus$, SO$_3^\ominus$
m (avg)=2-100; n (avg)=2-200
R1=C$_2$-C$_6$ Alkyl (preferably 2-3)
R2=CH$_3$, CH$_2$CH$_3$; x=1, 2

In another embodiment polymerases are stabilized using cationic polypropylene oxide/polyethylene oxide block copolymer surfactants based on alkyl diamines (for example TETRONIC® surfactants). The following general structures are exemplary:

(III)

m (avg)=2-100; (avg) n=2-200
R1=C$_2$-C$_6$ Alkyl (preferably 2-3)
R2=CH$_3$, CH$_2$CH$_3$; x=1, 2.

In another aspect, the TETRONIC® surfactants are modified to an amine oxide and the amine oxide form is used for stabilization. In particular TETRONIC® 1107 amine oxide was found to be particularly preferred. (TETRONIC® 1107 is tetrafunctional, ethoxylated and propoxylated ethylenediamine block copolymer surfactant, which has a cloud point (10% aqueous solution) greater than 100° C., an average molecular weight of 15000, a specific gravity of 1.04 at 25° C., a viscosity of 1100 cps at 77° C. and a melt point of 51° C.).

In another embodiment polymerases are stabilized using nonionic polypropylene poloxamers, for example, the PLURONIC® surfactants. The following general structure is exemplary:

(IV)

m (avg)=2-100 and n (avg)=2-200.

In one aspect the general structure of the surfactant additive is an amine oxide ylide or zwitterion derived from polyethoxylated alkylamines having the general structure:

where Q=—O$^\ominus$ or —(CH$_2$)$_p$Y, where p=1-6 and Y=CO$_2$—, SO$_3$—, PO$_3$H—; OSO$_3$—, or OPO$_3$H—;
m+n=2-200 (preferably 5-50):
x=1 or 2;
R1=C$_8$-C$_{20}$ Alkyl (eg., —(CH$_2$)$_n$CH$_3$)
R2=CH$_3$, CH$_2$CH$_3$, CH$_2$OCH$_3$, CH$_2$CH$_2$OCH$_3$, or CH$_2$CH$_2$OH, and
R3=CH3, CH$_2$OH, CH$_2$CH$_3$, CH$_2$OCH$_3$, CH$_2$CH$_2$OCH$_3$, or CH$_2$CH$_2$OH.

In another aspect, the surfactant has the following general structure:

where m+n=2-200 (preferably 5-50); x=1-2
R1=C$_8$-C$_{24}$ Alkyl (e.g. —(CH$_2$)$_n$CH$_3$)
R2=CH$_3$, CH$_2$CH$_3$, CH$_2$OCH$_3$, CH$_2$CH$_2$OCH$_3$ or CH$_2$CH$_2$OH
R3=CH$_3$, CH$_2$CH$_3$, CH$_2$OCH$_3$, CH$_2$CH$_2$OCH$_3$ or CH$_2$CH$_2$OH
R4=CH$_3$, CH$_2$OH, CH$_2$CH$_3$, CH$_2$OCH$_3$, or CH$_2$CH$_2$OCH$_3$.

In another aspect, the surfactant has the following general structure:

where m+n=2-200 (preferably 5-50); x=1-2
R1=C$_8$-C$_{24}$ Alkyl (e.g. —(CH$_2$)$_n$CH$_3$)
R2=CH$_3$, CH$_2$CH$_3$, CH$_2$OCH$_3$, CH$_2$CH$_2$OCH$_3$ or CH$_2$CH$_2$OH
R3=CH$_3$, CH$_2$CH$_3$, CH$_2$OCH$_3$, CH$_2$CH$_2$OCH$_3$ or CH$_2$CH$_2$OH
R4=CH$_3$, CH$_2$OH, CH$_2$CH$_3$, CH$_2$OCH$_3$, or CH$_2$CH$_2$OCH$_3$.

In another aspect, the surfactant has the following general structure:

Q=—O$^\ominus$; or —(CH$_2$)$_p$Y, where p=1-6, and Y=CO$_2^-$, SO$_3^-$, PO$_3$H$^-$, OSO$_3^-$, OPO$_3$H$^-$;
m+n=2-200 (preferably 5-50); x=1-2
R1=C$_8$-C$_{24}$ Alkyl (e.g. —(CH$_2$)$_n$CH$_3$)
R2=CH$_3$, CH$_2$OH, CH$_2$CH$_3$, CH$_2$OCH$_3$, or CH$_2$CH$_2$OCH$_3$.

Example 1

Amine oxide derivatives of selected surfactants were prepared as follows: amine containing surfactants (10 mmole in amine equivalents) were dissolved in ~3-4 volumes of ethanol. H$_2$O$_2$ (30%; 2.3 ml; 20 mmole) was added, and the solution stirred at 55° C. for 24-48 hrs. After cooling to room temperature, ~20 mg of 10% Pt° on C (platinum on activated carbon) was added, and stirring continued for another 4 h to decompose the excess peroxide. The solution was filtered through celite and evaporated under vacuum. The $^1$H-NMR was recorded in MeOH-d$_4$.

The procedure above was used to prepare amine N-oxides from the following polyalkoxylated amine surfactants: PEO (15) Laurylamine (DeThoxamine C-15, Deforest); PEO(5) Isodecyloxypropylamine (Tomamine E-14-5, Air Products); PEO(5) Isotridecyloxypropylamine (Tomamine E-17-5, Air Products); PEO(5) Stearylamine; PEO(10) Stearylamine; PEO(15) Stearylamine; PEO(50) Stearylamine;

TETRONIC® 304 (MW 1650); TETRONIC® 904; and TETRONIC® 1107. When using "PEO(X)" herein the (X) is the number of moles of ethylene oxide.

For testing, several additional amine oxide surfactants were obtained directly from commercial sources, including MACAT AO-12-2 (N,N-Bis(2-hydroxyethyl)laurylamine N-Oxide, available from Mason Chemicals) which is an ylide lacking the PEO groups and having the following structure:

TOMAMINE® AO-405 Surfactant (Air Products) (Polyethoxylated/Polypropoxylated (isodecyloxypropyl)amine N-Oxide (CAS #218141-38-9), falls into a series of amine oxide compounds available from Air Products under the brand name TOMAMINE® and having the general structure:

and Lauryldimethylamine N-oxide (available from Anatrace):

PEO(10) Stearyl (3-sulfo-propyl)-ammonium was prepared as follows: a mixture of propanesultone (0.36 g, 3 mmole) and PEO(10) Stearylamine (1.6 g, 2 mmole) was stirred in a sealed vial at 50-55° C. for 24 hr, producing a viscous yellow oil. Ethanolamine (0.12 ml, 2 mmole) was added and stirring continued at 50-55° C. for another 24 hr to quench the unreacted propanesultone. The $^1$H-NMR was recorded in MeOH-$d_4$.

Example 2

In order to test the efficacy of detergents on Taq DNA Polymerase, a stock of Taq DNA Polymerase at a base concentration of 111 units/ul was diluted to 5 units/ul in a storage buffer that lacked detergents. The standard Taq DNA Polymerase storage buffer has 0.5% Tween-20 and 0.5% NP-40. In this example 0.625 units of Taq were added per 25 ul reaction, so that represents a change in final detergent concentration of 0.0025% each detergent to 0.00011% of each. A 455 bp single-copy target from the human numb gene was PCR-amplified from 1 ng human genomic DNA in a 25 ul reaction with 0.625 units of the diluted Taq DNA polymerase. The cycling conditions were 95° C. for 2 minutes; 35 cycles of 95° C. for 10 seconds, 55° C. for 20 seconds, and 72° C. for 30 seconds; 72° C. for 5 minutes; and 10° C. until required. An aliquot of 10 ul was run on a 1.5% agarose/ethidium bromide gel.

Figure 1:
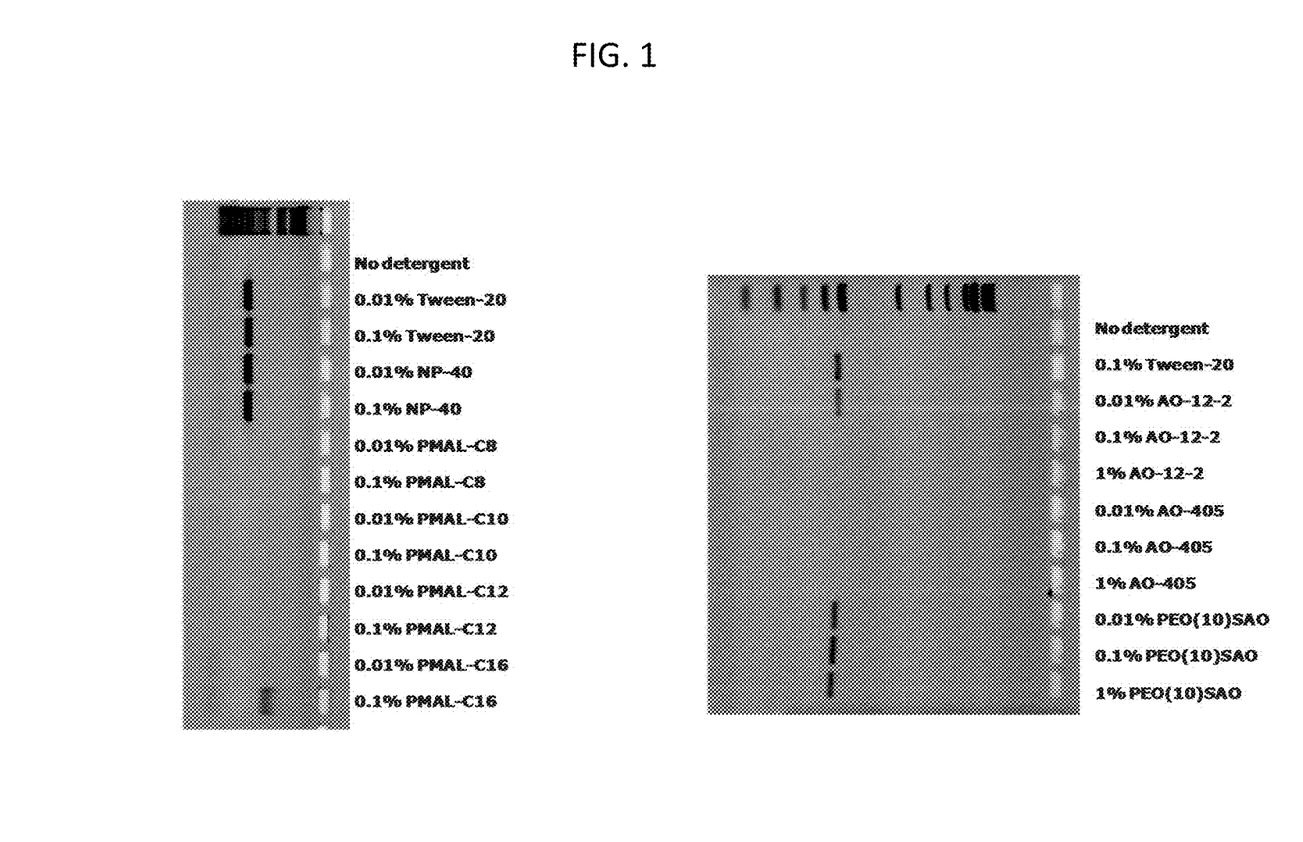
FIG. 1 shows a gel image of products of PCR in the presence of different non-ionic and zwitterionic detergents.

In FIG. 1, the results of the initial screen of several non-ionic and zwitterionic detergents are shown. In this example there is residual Tween-20 and NP-40 in the enzyme storage buffer. The concentrations of surfactants listed are the final concentration of that surfactant in the assay. All conditions in the example, including the "no detergent" condition, have 0.00011% Tween-20 and 0.00011% NP-40 resulting from carry-over from the enzyme storage buffer. As can be seen from the "no detergent" lanes on both gels, the carry over is not sufficient to promote the production of a visible PCR product of the expected size. As expected Tween-20 and NP-40 worked when present at 0.01% and 0.1%. PMAL-C8, -C10, -C12 or -C16, which are zwitterions but do not contain PEO did not. A0-12-2 worked at 0.01% and PEO(10) SAP worked at 0.01, 0.1 and 1%. It is clear that in addition to the standard non-ionic detergents with $PEO_n$, a zwitterionic or ylide with that polymer will also contribute to PCR product generation.

AO-12-2 is Dihydroxyethyl Cocamine Oxide; AO-405 is Polyethoxylated/Polypropoxylated (isodecyloxypropyl) amine N-Oxide; and PEO(10)SAO is Polyethoxylated (10) Stearylamine N-Oxide. The AO-12-2 resulted in a product at 0.01% but not at 0.1 or 1%. AO-405 results in no visible product. The PEO(10)SAO at between 0.01% and 1% showed similar amounts of product as the inclusion of 0.1% Tween-20. The number in parenthesis (X) refers to the average total number of ethylene oxide units, so if there are two PEO groups and X is 5 then the average length (n) is 2.5.

Figure 2:
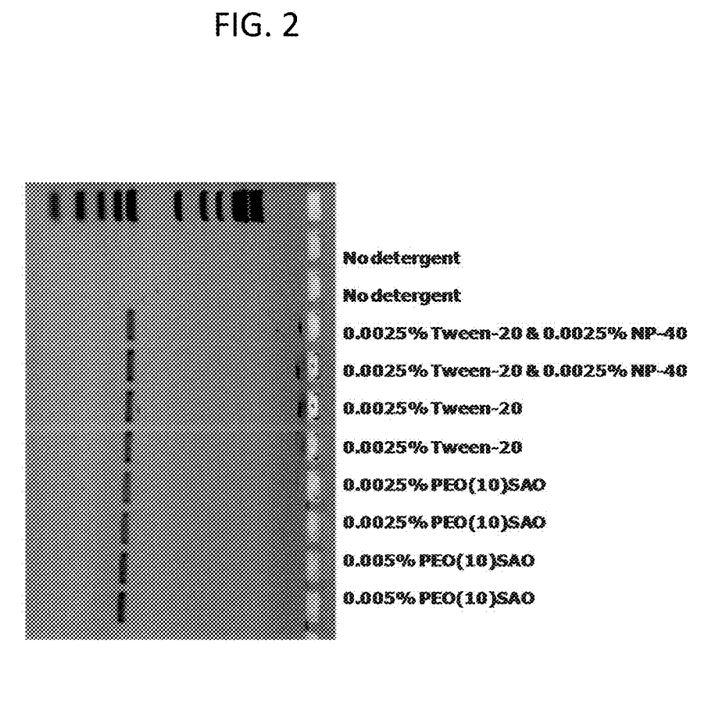
FIG. 2 shows a gel image of products of PCR in the presence of varying amounts of a $PEO_n$ detergent or non-ionic detergents Tween-20 and NP-40 with detergent-free Taq DNA Polymerase.

PMAL®-C12 is Poly (Maleic Anhydride-alt-1-Tetradecene) substituted with 3-(Dimethylamino) Propylamine and has the following structure:

PMAL®-C8 is Poly (Maleic Anhydride-alt-1-Decene) substituted with 3-(Dimethylamino) Propylamine and has the following structure:

PMAL®-C16 is Poly (Maleic Anhydride-Alt-1-Octadecene) substituted with 3-(Dimethylamino) Propylamine and has the following structure:

Because a small amount of Tween-20 and NP-40 was carried over in the previous experiment, Taq DNA Polymerase was purified without the addition of detergents after the lysis step to provide a "detergent-free" Taq for use in the next example. The previous numb target and reaction conditions were used with 0.625 units of Taq per reaction. As can be seen in FIG. 2, without detergent no PCR product is generated while both non-ionic and zwitterionic surfactants with $PEO_n$ groups generate product.

Figure 3:
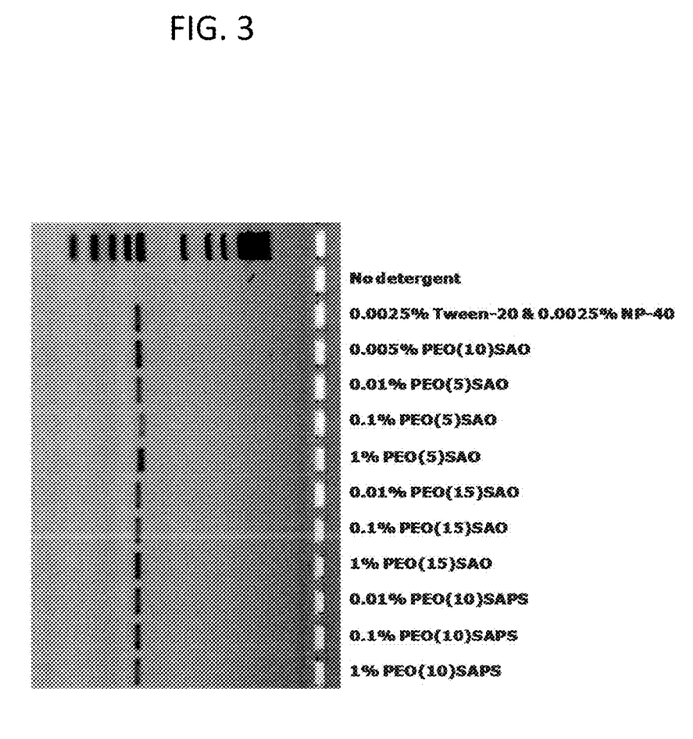
FIG. 3 shows a gel image of $PEO_n$ length and zwitterion variations with "detergent-free" Taq DNA Polymerase.

The results shown in FIG. 3, demonstrate that $PEO_n$ of different lengths and using amine-sulfoxide as the zwitterion rather than amine-oxide also led to positive results using detergent-free Taq DNA Polymerase.

Figure 4:
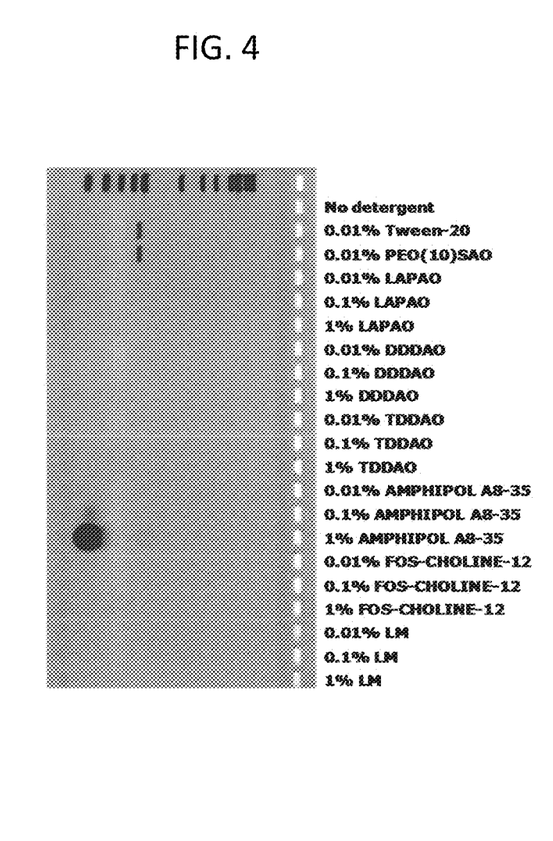
FIG. 4 shows a gel image of various zwitterionic detergents without $PEO_n$ groups and a non-ionic, non-polymeric detergent (lauryl maltoside) with "detergent-free" Taq DNA Polymerase.

PEO(X)SAO is polyethyoxylated (X) stearylamine N-oxide, where X is the sum of the number of PEO groups, and has the general structure:

and PEO(X)SAPS is polyethyoxylated (X) Stearylammoniumpropylsulfonic acid, inner salt and has the general structure:

Because the results demonstrate that PEO polymeric groups are useful in the methods, detergent-free Taq was tested using the same assay against various other detergents without $PEO_n$ groups. The results are shown in FIG. 4 and demonstrate the need for a specific type of polymer surfactant. Note that the band in the Amphipol lane is background fluorescence. FIG. 4 shows the results of testing other zwitterionic detergents without $PEO_n$ groups and a non-ionic, non-polymeric detergent, lauryl maltoside, with detergent-free Taq DNA Polymerase. LAPAO is 3-Dodecylamido-N,N'-dimethylpropyl amine oxide DDDAO is n-dodecyl-n,n-dimethylamine-n-oxide;

TDDAO is n-tetradecyl-n,n-dimethylamine-n-oxide;

FOS-CHOLINE® is n-Dodecylphosphocholine;

and

LM is Lauryl maltoside

As can be seen from the results, PCR product was observed in the presence of the non-ionic detergent Tween-20 and in the presence of the PEO(10)SAO, but not when the other detergents lacking $PEO_n$ groups were tested.

Figure 5:
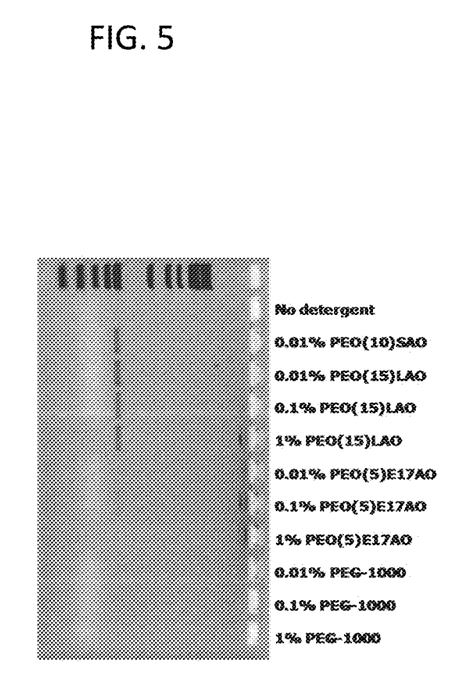
FIG. 5 shows a gel image of PCR products from reactions that include various alkyl chains with $PEO_n$ groups and a polyethylene glycol.

FIG. 5 shows the effect of different alkyl groups on zwitterionic amine-oxide derivatives as well as polyethylene glycol (chain length 1000) "PEG-1000". The data indicates that PEG-1000 does not function as a stabilizer, suggesting that micelle formation may be important for stabilization.

Figure 6:
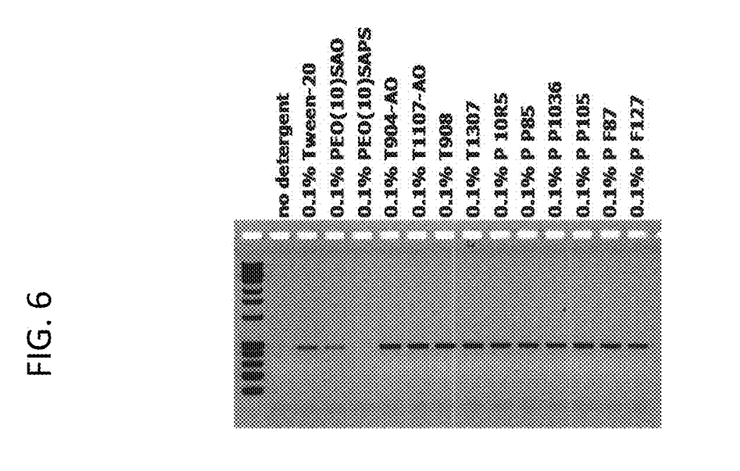
FIG. 6 shows a gel image of PCR products from reactions that included blocked co-polymers under extreme conditions with detergent-free Taq DNA Polymerase.

To further test the effectiveness of $PEO_n$-derivatives, the denaturation temperature was changed from 95° C. to 98° C. in the cycling protocol. This increase in temperature adds additional stress to the function of Taq DNA Polymerase. A selection of PLURONIC® and TETRONIC® surfactants were tested (labels in the figures are abbreviated, for example, "T908" refers to TETRONIC® 908 and "P F87" refers to PLURONIC® F87). In addition, TETRONIC® 904 and 1107 were modified to amine-oxide, forms and then tested. FIG. 6 shows that not only are blocked co-polymers effective, the amine-oxide TETRONIC® derivatives also function as thermal stabilizers of DNA polymerases.

In some aspects surfactants are selected for use in the methods because they have a cloud point (temperature at which the solid begins to precipitate and give the fluid a cloudy appearance) greater than or equal to 80° C., greater than or equal to 90° C. and in particularly preferred aspects the cloud point is greater than about 100° C. (in each case when measured at about 1% aqueous). The cloud point is the temperature above which a surfactant solution separates into a detergent rich phase and a detergent poor phase (see, Rosen et al. Surfactants and interfacial Phenomena, $3^{rd}$ ed. 2004, Hoboken; John Wiley & Sons, Inc. and Neugebauer, J. M. Detergents: an overview, *Methods Enzymol,* 1990, 182, p. 239-53). The separation is visualized as turbidity within the solution. An increase in temperature favors micelle formation; the rapid growth of micelles along with intermicellar attraction likely results in the formation of large particles that can precipitate out of solution, thus causing turbidity. This phase separation is reversible upon cooling. Nonpolar additives (i.e., hydrocarbons) tend to increase the cloud point whereas polar compounds (i.e., alcohols) and salts tend to decrease the cloud point. For stabilization of thermal stable enzymes that are used for PCR, which typically includes a denaturation step above 90° C., higher cloud points are desirable.

The amine oxide detergents of the present invention have higher cloud points than their non-amine oxide counterparts. For example, PEO(10)stearlyamine has a cloud point of 60° C. compared to PEO(10)stearylamine N-oxide's cloud point of greater than 100° C., in both cases when measured at about 1% detergent concentration in 6xSSPE buffer. In some aspects detergents with cloud points above 90° C. are preferred.

Table 1 summarizes the surfactants or blocked co-polymers that worked in the assay used and those that did not.

| Surfactant | Function | AO | Y/Z/NI | PEO groups |
|---|---|---|---|---|
| Tween 20 | YES | NO | NI | NO |
| NP 40 | YES | NO | NI | NO |
| PE0 (5) SAO | YES | YES | Y | YES |
| PE0 (10) SAO | YES | YES | Y | YES |
| PEO (15) SAO | YES | YES | Y | YES |
| PEO(10) SAPS | YES | NO | Z | YES |
| PEO(5) LAO | YES | YES |  | YES |
| TETRONIC ® 304 | YES | NO | Y/Z | YES |
| TETRONIC ® 1107 | YES | NO | Y/Z | YES |
| TETRONIC ® 904 AO | YES | YES | Y/Z | YES |
| TETRONIC ® 1107 AO | YES | YES | Y/Z | YES |
| TETRONIC ® 908 | YES | NO | Y/Z | YES |
| TETRONIC ® 1307 | YES | NO | Y/Z | YES |
| PLURONIC ® P85 | YES | NO | NI | YES |
| PLURONIC ® 10R5 | YES | NO | NI | YES |
| PLURONIC ® L35 | YES | NO | NI | YES |
| PLURONIC ® L64 | YES | NO | NI | YES |
| PLURONIC ® P65 | YES | NO | NI | YES |
| PLURONIC ® P84 | YES | NO | NI | YES |
| PLURONIC ® P1036 | YES | NO | NI | YES |
| PLURONIC ® P103 | YES | NO | NI | YES |
| PLURONIC ® P104 | YES | NO | NI | YES |
| PLURONIC ® P105 | YES | NO | NI | YES |
| PLURONIC ® P123 | YES | NO | NI | YES |
| PLURONIC ® F68 | YES | NO | NI | YES |
| PLURONIC ® F77 | YES | NO | NI | YES |
| PLURONIC ® F87 | YES | NO | NI | YES |
| PLURONIC ® F127 | YES | NO | NI | YES |
| AO-12-2 | NO | YES | Y | NO |
| AO-405 | NO | YES | Y | YES |
| LAPAO | NO | YES | Y | NO |
| DDDAO | NO | YES | Y | NO |
| TDDAO | NO | YES | Y | NO |
| Amphipol A8-35 | NO | NO | Z | NO |
| Lauryl Maltoside | NO | NO | NI | NO |
| PEG-1000 | NO | NO | NI | YES |
| PEO (5) E17 AO | NO | YES | Z | YES |
| TETRONIC ® 304-AO | NO | YES | Z | YES |
| FOS-CHOLINE ® -12 | NO | NO | Z | NO |
| PMAL ® -C8 | NO | NO | Z | NO |
| PMAL ® -C10 | NO | NO | Z | NO |
| PMAL ® -C12 | NO | NO | Z | NO |
| PMAL ® -C16 | NO | NO | Z | NO |

In some aspects, the stabilization of thermostable polymerases using the compounds disclosed herein are combined with methods for modifying thermostable polymerases to be inactive until activated by heating. Specifically, methods for inactivating polymerases until they are heated for at least 10 minutes at a temperature at or above 50° C. are disclosed. Inhibiting the activity of thermostable polymerases at lower temperature is known to mitigate non-specific amplification that can generate non-specific primer extension products that compete with amplification of the desired target sequences. This non-specific amplification can decrease the efficiency of the amplification of the desired target. Problems caused by non-specific amplification are discussed in Chou et al., 1992, Nucleic Acids Research 20(7):1717-1723, incorporated herein by reference. See also, Birch et al. U.S. Pat. No. 5,677,152, which is incorporated herein by reference.

Non-specific amplification can be reduced by reducing the formation of extension products from primers bound to non-target sequences prior to the start of the reaction. Several strategies have been developed for minimizing non-specific extension. These methods, referred to as a "hot-start" approaches, generally rely on withholding one or more reagent until the temperature is raised sufficiently to provide the necessary hybridization specificity. Some hot-start methods use a heat labile material, such as wax, to separate or sequester reaction components (see, U.S. Pat. No. 5,411,876). Another method of reducing the formation of non-specific extension products relies on inhibition of the DNA polymerase using a compound which non-covalently binds to the DNA polymerase in a heat-reversible manner. U.S. Pat. No. 5,338,671, describes polymerase inactivation by the use of antibodies specific for a thermostable DNA polymerase. The antibodies are incubated with the DNA polymerase to allow formation of the antibody-DNA polymerase complex. Antibody inhibition of DNA polymerase activity is inactivated by a high temperature pre-reaction incubation.

Another hot-start method uses the non-covalently binding of a compound to the primers in a heat-reversible manner, thereby preventing the primers from hybridization to any sequence, target or otherwise. For example, single-stranded binding protein added to a reaction mixture will bind the primers, thereby preventing primer hybridization and inhibiting primer extension. Improvements in the yield of PCR products using gene 32 protein are described in Schwarz et al., 1990, Nucleic Acids Research 18(4):10.

Other hot-start methods rely on a reaction between the enzyme and a modifier reagent, which results in a reversible chemical modification of the enzyme, resulting in the loss of all, or nearly all, of the enzyme activity. The modification consists of the covalent attachment of the modifier group to the protein. The modifier compound is chosen such that the modification is reversed by incubation at an elevated temperature in the amplification reaction buffer. The use of 2,3-substituted maleic anhydrides for such inactivation has been disclosed, see U.S. Pat. No. 5,773,258.

The methods disclosed herein are similar to those of the methods disclosed in U.S. Pat. No. 5,773,258, but involve incubating the polymerase in the presence of 2-(Methylsulfonyl)ethyl 4-nitrophenyl carbonate (MSEC) under conditions where lysines in the polymerase are modified reversibly. The modification is reversed, activating the enzyme, by heating for about 5-10 min at a temperature above 50° C., preferably at a temperature of about 90 to 95° C. and more preferably about 95° C. Typical reaction conditions for PCR may be (i) 5 min at 95° C., (ii) 15 sec at 95° C., (iii) 60 sec at 60° C., (iv) 2 min at 68° C., (v) repeat steps (ii), (iii) and (iv) 35 times, (vi) 10 min at 68° C. The reaction conditions for the PCR using the MSEC modified enzyme may also contain 5 mM-500 mM betaine. The dNTP concentration in the reaction is may be about 100-400 uM of each of four dNTPs, (dATP, dGTP, dTTP and dCTP). In one aspect the reaction conditions are 40 mM Tricine-KOH pH 8.0, 16 mM KCl, 3.5 mM MgCl2, 3.75 ug/ml BSA, 400 mM betaine, 1.4 mM dNTP (350 uM of each) and 2.5 to 30U enzyme in a 50 ul reaction. In one aspect the enzyme is present in the reaction at about 0.25 units per ul. In another aspect, the reaction contains 20 mM EPPS, pH 8.5, 50 mM NaOAc, 3.5 mM MgCl2, 5% glycerol, 0.01% Tetronic-AO-1107, 400 uM each of dATP, dTTP, dGTP and dCTP, and about 0.005 mg/ml modified enzyme. Primer concentration may be 0.1 uM each primer for products greater than 500 bp in length or 0.2 uM each primer for products less than 500 bp in length. Betaine may also be added to the reaction under any of the disclosed reaction conditions, preferably to about 400 mM. In another aspect the PCR may be set up as follows:

| Reagents | A (μl) | B (μl) | C (μl) | Final Conc. |
|---|---|---|---|---|
| Nuclease-free water | 33.75 | 33.75 | 33.0 | |
| 10X PCR Reaction Buffer 1 (71165) | 5 | | | 1X |
| 10X PCR Reaction Buffer 2 (74155) | | 5 | | 1X |
| PCR Nucleotide Mix (10 mM) | 1 | 1 | 1 | 200 μM ea |
| Taq DNA Polymerase (5 U/μL) | 0.25 | | | 2.5 units |
| Exo-free Taq DNA Polymerase (5 U/μL) | | 0.25 | | 2.5 units |
| MSEC Taq DNA Polymerase (12.5 U/μL) | | | 1 | 12.5 units |
| Forward/λ Primer #1 (10 μM) | 2.5 | 2.5 | 2.5 | 0.5 μM |
| Reverse/λ Primer #2 (10 μM) | 2.5 | 2.5 | 2.5 | 0.5 μM |
| DNA Template (1 ng/μl) | 5 | 5 | 5 | 10 ng |
| Total volume | 50 | 50 | 50 | |

Three classes of protecting groups were evaluated: 2,3-substituted maleic anhybrides, alpha-activated compounds that can undergo beta-elimination and molecules that can undergo intramolecular cyclic displacement or assisted elimination. The experimental compounds had the general structure:

Where Y could be N-hydroxysuccinimide (NHS), p-nitrophenol (pNP), or imidazole and X could be $CONMe_2$, $MeSO_2$, CN, $NO_2$, $CO_2Me$, $(CH_2)_2SMe$, $N(CH_3)CHO$, or $CH_2C(O)CH_3$. The reactivity was tested in Tris pH 8 or Tricine pH 8.8. Buffer pH measurements are at room temperature (~25° C.). The compound found to be most effective of the test compounds was 2-(Methylsulfonyl)ethyl 4-nitrophenyl carbonate or MSEC. MSEC has the following structure:

The MSEC modifies lysines in the enzyme. The enzyme to be modified is preferably a thermostable DNA polymerase and may be a 5' exonuclease domain deletion mutant (exo–), e.g. of Taq DNA polymerase (exo–), or may retain the 5' exonuclease domain (exo+). In preferred aspects MSEC is used to reversibly modify Taq DNA polymerase. To inactivate the Taq DNA polymerase an appropriate volume of a freshly prepared 100× solution (120 mM) of MSEC (SIGMA PN 69227) is added to a 1 mg/ml solution of Taq in acylation buffer (100 mM Bicine pH 8.5, 1 mM EDTA, 100 mM KCl). The MSEC solution should preferably be added to the Taq within about 5 min of preparation as it degrades over time. After adding the MSEC solution to the Taq the solution is mixed by inverting, preferably end over end about 5 times, and then placed in a 25° C. incubator for 2 hours without rotating or stirring. The MSEC reaction with lysines results in a change of the buffer to a yellow color. Following this incubation the Taq is dialyzed against transition buffer (20 mM EPPS pH 7.5, 100 mM KCl, 0.1 mM EDTA, 1% Tetronic-AO, 10% glycerol and 1 mM DTT) and then against a final buffer (20 mM EPPS pH 7.5, 100 mM KCl, 0.1 mM EDTA, 1% Tetronic-AO, 50% glycerol and 1 mM DTT).

In another aspect FRET-based molecules to be used as passive reference dyes for qPCR are included in the reaction mixture. The sample being amplified in a PCR reaction may contain one or more types of dye molecules that serve as a "passive" reference having some fluorescence in the same wavelength range as the DNA binding dye. This reference dye is made up, for example, of a nucleic acid sequence labeled with Rhodamine and Fluorescein dye derivatives. These passive dye molecules do not take part in the PCR reaction, so that their fluorescence is substantially without influence from DNA and remains constant during the reaction. This fluorescence can be used to normalize the fluorescence from the DNA binding dye with a standard concentration of passive dye included in the ingredients of at least one vial, preferably in every vial. Passive reference dyes have been described, for example, in U.S. Pat. No. 6,818,437. The dye is used as an internal reference for fluorescent signal normalization and correction of well-to-well optical variation and pipetting errors. The dye is preferably matched to the excitation optics of the instrument being used. The dye may be made available in a solution, for example a 25 um solution, and may be in a buffer, for example, 10 mM Tris-HCl (pH 8.6), 0.1 mM EDTA and 0.01% Tween-20.

In preferred embodiments the compounds will be compatible with a broad range of commercial qPCR platforms, molecules will preferably exhibit good solubility, thermal stability, and efficient and stable 488 nm excitation and 610 nm emission characteristics under typical conditions used in RT PCR. The molecules of this invention consist of combinations of a fluorescein (FAM) or FAM analog as the donor dye and a rhodamine-101 (ROX) or ROX analog as acceptor dye, the two being connected by a stable covalent attachment to allow efficient FRET. The following molecules were evaluated. The first compound was referred to as "Dye 592" and has structure:

$C_{50}H_{37}B_2F_4N_7Na_2O_{11}S_2$
Mol. Wt.: 1119.60

The second was FRET Dye 1 where the donor is 6FAM and the acceptor is ROX. The structure is:

FRET Dyes 2-4 where the donor is 6-FAM and the acceptor is CalFluorRed 610 with structures:

2 B = H
3 B = 5-methyluracil

What is claimed is:

1. A composition comprising a thermostable polymerase that has been reversibly modified with a polymerase-modifying reagent of the following structure:

$$Y-C(=O)-O-CH_2CH_2-X$$

wherein Y=N-hydroxysuccinimide (NHS), p-nitrophenol (pNP) or imidazole;

X=CONMe$_2$, MeSO$_2$, CN, NO$_2$, CO$_2$Me, (CH$_2$)$_2$SMe, N(CH$_3$)CHO, or CH$_2$C(O)CH$_3$;

and a zwitterionic amine oxide.

2. The composition of claim 1, wherein the zwitterionic amine oxide has at least one polyethylene oxide (PEO) group.

3. The composition of claim 1, wherein the zwitterionic amine oxide has a fatty alkyl group.

4. The composition of claim 1, wherein the zwitterionic amine oxide has the following structure:

$$(R1)-N^{\oplus}(Q)(R2)_{2-x}-[(CH_2CH(R3)O)_m-(CH_2CH_2O)_n-H]_x$$

where Q=—O$^{\ominus}$; or —X—Y, where X=C$_1$-C$_3$ alkyl and Y=CO$_2^{\ominus}$, SO$_3^{\ominus}$;

m+n=2-200;

R1=C$_1$-C$_{30}$ alkyl

R2=CH$_3$, CH$_2$CH$_3$; x=1, 2

R3=H, CH$_3$, or CH$_2$OH.

5. The composition of claim 4 wherein m+n is 5 to 50.

6. The composition of claim 1 wherein the zwitterionic amine oxide is a tetrafunctional, ethoxylated and propoxylated ethylenediamine block copolymer surfactant modified to an amine oxide.

7. The composition of claim 1, wherein the zwitterionic amine oxide has the following structure:

[structure with PEO$_n$—PPO$_m$ and PPO$_m$—PEO$_n$ groups connected via N$^{\oplus}$—O$^{\ominus}$]

wherein m≥1 and n≥1 and wherein PEO=polyethylene oxide and PPO=polypropylene oxide.

8. The composition of claim 1, wherein the polymerase-modifying reagent is 2-(methylsulfonyl)ethyl 4-nitrophenyl carbonate (MSEC).

9. The composition of claim 1 wherein the thermostable polymerase is Taq DNA polymerase.

10. The composition of claim 1, wherein the zwitterionic amine oxide has the following structure:

[structure with PEO$_n$—PPO$_m$ and PPO$_m$—PEO$_n$ groups connected via N$^{\oplus}$—O$^{\ominus}$]

wherein m≥1 and n≥1 and wherein PEO=polyethylene oxide and PPO=polypropylene oxide;

wherein the polymerase modifying reagent is 2-(methylsulfonyl)ethyl 4-nitrophenyl carbonate (MSEC); and wherein the thermostable polymerase is Taq DNA polymerase.

* * * * *

UNITED STATES PATENT AND TRADEMARK OFFICE
CERTIFICATE OF CORRECTION

PATENT NO. : 9,085,761 B1  
APPLICATION NO. : 13/791164  
DATED : July 21, 2015  
INVENTOR(S) : Glenn H. McGall, Anthony D. Barone and Christopher J. Kubu Page 1 of 1

It is certified that error appears in the above-identified patent and that said Letters Patent is hereby corrected as shown below:

In the specification

At line 11 of Column 7 of the patent, please amend "$Y=CO_3^{\ominus}$" (in equation II) to read "$Y=CO_2^{\ominus}$".

At line 47 of Column 7 of the patent, please amend "$O-)_n(-CH_2CH_2O-_n -H)$" (in equation IV) to read "$O-)_m(-CH_2CH_2O-)_n -H)$".

Signed and Sealed this
Fifteenth Day of December, 2015

Michelle K. Lee
*Director of the United States Patent and Trademark Office*